United States Patent [19]

Cole

[11] Patent Number: 4,483,921
[45] Date of Patent: * Nov. 20, 1984

[54] IMMUNOASSAY WITH ANTIGEN OR ANTIBODY LABELED LIPOSOMES SEQUESTERING ENZYME

[75] Inventor: Francis X. Cole, Stow, Mass.

[73] Assignee: Collaborative Research, Inc., Lexington, Mass.

[ * ] Notice: The portion of the term of this patent subsequent to Aug. 3, 1999 has been disclaimed.

[21] Appl. No.: 372,756

[22] Filed: Apr. 28, 1982

Related U.S. Application Data

[63] Continuation of Ser. No. 222,815, Jan. 12, 1981, Pat. No. 4,342,826, which is a continuation-in-part of Ser. No. 117,864, Feb. 4, 1980, abandoned.

[51] Int. Cl.$^3$ .................................... G01N 33/54
[52] U.S. Cl. ........................ 435/7; 435/177; 435/182; 435/188; 435/810; 436/536; 436/537; 436/829
[58] Field of Search ............... 435/4, 7, 177, 180, 435/182, 188, 810; 436/536, 537, 826, 829

[56] References Cited

U.S. PATENT DOCUMENTS

| | | | |
|---|---|---|---|
| 3,850,578 | 11/1974 | McConnell | 436/829 |
| 3,887,698 | 6/1975 | McConnell et al. | 436/829 |
| 3,937,668 | 2/1976 | Zolle | 252/316 |
| 4,021,364 | 5/1977 | Speiser et al. | 252/316 |
| 4,062,799 | 12/1977 | Matsukawa et al. | 436/829 |
| 4,066,568 | 1/1978 | Nakazawa et al. | 436/829 |
| 4,078,052 | 3/1978 | Papahadjopoulos et al. | 424/36 |
| 4,193,983 | 3/1980 | Ullman et al. | 436/829 |
| 4,235,792 | 11/1980 | Hsia et al. | 424/12 |
| 4,235,871 | 11/1980 | Papahadjopoulos et al. | 424/19 |
| 4,241,046 | 12/1980 | Papahadjopoulos et al. | 424/19 |
| 4,255,411 | 3/1981 | Lim et al. | 436/829 |
| 4,342,739 | 8/1982 | Kakimi et al. | 436/829 |
| 4,342,826 | 8/1982 | Cole | 435/7 |

OTHER PUBLICATIONS

Strejan et al, "Naturally Occurring Antibodies to Liposomes", *J. Immunol.*, vol. 123, No. 1, (1979), pp. 370-378.

Uemura et al, "Activities vs. Passive Sensitization of Liposomes Toward Antibody and Complement by Ditrophenyl Derivatives of Phosphatidyl Ethanolamine", *Biochem.*, vol. 11, No. 22, (1972), pp. 4085-4094.

Kataoka et al, "Release of Macromolecular Markers (Enzymes) from Liposomes Treated with the Antibody and Complement", *Biochim. Biophys. Acta.*, vol. 293, No. 2, (1973), pp. 158-179.

Rosenthal et al, "Evaluation of Enzyme-Multiplied Immunoassay Technique (EMIT) for Determination of Serum Digoxin", *Clin. Chem.*, vol. 22, No. 11, (1976), pp. 1899-1902.

Wei et al, *J. Immunol. Methods*, vol. 9, (1975), pp. 165-170.

Rosenquist et al, *J. Immunol. Methods*, vol. 15, (1977), pp. 147-155.

Chan et al, *J. Immunol. Methods*, vol. 21, (1978), pp. 185-195.

Aaga et al, *Biochem. Biophys. Res. Comm.*, vol. 95, (1980), pp. 187-192.

Shiba et al, "Thin-Layer Potentiometric Analysis of Lipid Antigen-Antibody Reaction by Tetrapentylammonium (TPA+) TPA Ion Selective Electrode", *Anal. Chem.*, vol. 52, No. 11, (1980), pp. 1610-1613.

Gregoriadis et al, *Liposomes in Biological Systems*, 156, 158, 159, & 174-178.

Smolasky et al, *J. Immunol. Methods*, vol. 15, (1977), pp. 255-265.

D'Orazlo et al, *Anal. Chem.*, vol. 49, (1977), pp. 2083-2086.

*Primary Examiner*—Sidney Marantz
*Attorney, Agent, or Firm*—Wolf, Greenfield & Sacks

[57] ABSTRACT

An immunoassay method utilizes antigen tagged, enzyme encapsulating liposomes which are immunospecifically ruptured in the presence of cognate antibody and active complement. A homogeneous phase reaction occurs with the antibody and complement acting to release the enzyme if an immunospecific antigen-antibody complex is formed at the surface of the liposome. The positions of the antigen and antibody can be reversed.

32 Claims, No Drawings

IMMUNOASSAY WITH ANTIGEN OR ANTIBODY LABELED LIPOSOMES SEQUESTERING ENZYME

RELATED APPLICATION

This application is a continuation of application Ser. No. 222,815, filed Jan. 12, 1981, U.S. Pat. No. 4,342,826, which is a continuation-in-part of application Ser. No. 117,864 filed Feb. 4, 1980 (now abandoned).

BACKGROUND OF THE INVENTION

There has always been a need for high volume screening assays to identify the presence of antigenic materials, antibodies and analytes in a large number of different sampling situations. Various test methods have been used in the past including gas chromatography, mass spectrometry, liquid chromatography and various bioassay methods. Often these methods are time consuming, expensive and cannot be applied to large scale screening programs in an efficient manner.

It has been suggested that immunoassay methods could be used for such screening since immunoassays are known to be easily designed to be specific, highly sensitive and simple to perform. Radioimmunoassays for example have found a large market and use in connection with clinical diagnostics. However, RIA procedures are often incompatible with large scale screening programs. Radiotracers used have inherently limited stability and special disposal and personnel screening procedures are often required. Sophisticated instrumentation is often necessary. For certain uses RIA may create potential hazards as in food processing environments.

Other techniques have been developed such as fluorescent or enzymatic immunoassay techniques which are useful in that potentially hazardous reagents are avoided. However, often these methods require separation by filtration or centrifugation steps in procedures used. Such separations make test procedures inherently slower and difficult to automate.

In a more recent development, enzyme labeled antigen is used which requires no bound-free separation and thus can be performed quickly with excellent sensitivity. Such a system can be automated for high volume assays as in EMIT system disclosed by Rosenthal, A. F., Vargas, M. G. and Klass, C. S. (1976) Clin Chem. 22, 1899. This system utilizes a mode of coupling antigen to enzyme which is quite critical and can result in the system being not readily adapted to different analyses without extensive development for each new system.

Recently, there have been reports of liposomes which can carry enzymes or substrates and be labeled with antigens or antibodies. Liposomes labeled with antigens at their external surface and containing an enzyme entrapped in their internal volume are reportedly mixed with cognate antibody and complement to determine whether or not the liposomes permit release of the entrapped enzyme. This determination is reported made by detecting enzymatic activity which is physically released from the liposomes after separating liposomes from surrounding medium. See Uemura, K. and Kinsky, S. C. (1972) Biochemistry, 11, 4085-4094 and Kataoka, T., Williamson, J. and Kinsky, S. (1973) Biochemics et Biophysica Acta 298, 158-179. However, there has been no recognition that such liposomes when suitably formed with suitable high signal to noise ratios can be useful for immunoassay procedures which avoid the use of separation steps and permit testing in homogeneous phase reactions. Moreover there are reported difficulties in preparing prior art immunospecific liposomes, G. H. Strejan, P. M. Smith, C. W. Grant and D. Surlan, "Naturally Occurring Antibodies To Liposomes", The Journal of Immunology, Vol. 123, No. 1, July 1979, 370-378. Furthermore, it has long been established that diffusion of macromolecules such as enzymes through lesions produced by complement in bilayer membranes is very much slower than that of small molecules (Green, H., Barrow, P. and Goldberg, B. [1959] J. Exp. Med. 110, 699).

SUMMARY OF THE INVENTION

It is an object of this invention to provide immunoassay products and methods for use in rapid and simplified testing procedures which can quantitatively and/or qualitatively determine the presence or absence of antigenic materials or antibodies.

It is another object of this invention to provide methods in accordance with the preceding object which can be carried out by relatively untrained personnel with test results determined in a single step with ease of resulting readout and without the need for any separation step after the test reaction.

It is another object of this invention to provide a homogeneous phase reaction in which antigen or antibody-tagged enzyme-laden liposomes are immunospecifically caused to release enzyme in the presence of cognate antigen or antibody and active complement.

It is still another object of this invention to provide liposomes labeled with an antigen or antibody and carrying an enzyme yet having a signal to noise ratio no less than 10 and preferably having a stability of at least about 60 days when carried in a liquid.

According to the invention a liposome is labeled with an antigen or antibody and carries an enzyme, yet, has a signal to noise ratio of no less than 10. The enzyme is encapsulated within the liposome. Preferably the liposome is carried in a liquid media and is stable for a period of at least 60 days. Preferably the liposome signal to noise ratio is high and above 60. with stability over six months at 4° C. under inert gas atmosphere. In a kit form the liposome of this invention is sold along with vials of cognate antibodies or antigen which are immunospecific for the antigen or antibody attached to the surface of the liposome, and complement.

According to the method of this invention, an immunoassay method comprises forming a mixture of (a) liposomes labeled with an antigen or antibody carrying an enzyme and having a signal to noise ratio of no less than 10, (b) a substrate for said enzyme, (c) a test material to be tested for specific antigen or antibody activity and (d) complement. The mixture is observed and the presence of enzymatic activity detected as by color change visible to the eye, spectroscopic readout or the like. Preferably, additional cognate antigen or antibody as attached to the liposomes is admixed with the mixture and the test is carried out for the same antigen or antibody as is attached to the liposomes. If immunospecific antigen or antibody tested for, is present in the test material, the free antibody or antigen as the case may be, in the mixture reacts with that antigen or antibody leaving the liposome intact, thus preventing complement attack while if the cognate is not present in the test material the liposome label is reacted and enzyme activity becomes detectable. The amount of cognate in the test sample if present can permit some complement attack if insufficient to react with all of the free cognate in the test mixture, and a portion of the enzymatic activity can then be detected.

In some cases, the immunoassay method may be employed directly to detect any of the elements of the group antigen, antibody or complement. In the direct method an incomplete mixture lacking but one element of the group antigen, antibody or complement is prepared and the presence of the missing element in a test sample is assessed by the extent to which addition of the sample to the incomplete mixture promotes lysis of the liposome by immune specific attack on the liposomal membrane or exposure of the encapsulated enzyme to the fluid around the liposome. When the test material is to be tested for the cognate antibody or antigen to that which acts as a label for the liposome, no antigen or antibody need be added to the mixture. A direct immunoassay method for antigen or antibody would comprise a mixture of:

(a) liposomes labeled with one of an antigen or its cognate antibody, carrying an enzyme and having a signal to noise of no less than 10,
(b) a substrate for said enzyme,
(c) a test material to be tested for the one antigen or cognate antibody,
(d) complement.

If the aim of a direct immunoassay is to assess the active complement in a test sample the method would comprise a mixture of:

(a) liposomes labeled with one of an antigen or its cognate antibody, carrying an enzyme and having a signal to noise of no less than 10,
(b) a substrate for said enzyme,
(c) a test material to be tested for complement,
(d) free cognate of the other of said one antigen or antibody.

A preferred immunoassay method preferably comprises, forming a mixture of:

(a) liposomes labeled with one of an antigen or its cognate antibody carrying an enzyme and having a signal to noise ratio of no less than 10,
(b) a substrate for said enzyme,
(c) a test material to be tested for the one antigen or cognate antibody,
(d) complement, and
(e) free cognate of the other of said one antigen or antibody, and detecting the presence or absence of enzymatic activity in said mixture. In this method the antigen to be tested for can be used to label the liposomes and free cognate antibody used. Alternately the antibody to be tested for can be used to label the liposome and free cognate antibody used.

Preferably the method is carried out as a one-step method and all materials are added to a single vial with incubation at standard immunological conditions as for example 37° C., or in a range of from 4° C. to 45° C. for periods of from about 1 second to 120 minutes. Alternately all but the enzyme substrate are admixed and incubated for 5 to about 120 minutes or more and then this admixture is added to an enzyme substrate and the result determined.

A kit for detecting one of an antigen or its cognate antibody preferably has a first container carrying liposomes labeled with one of the antigen or its cognate antibody suspended in an appropriate buffer. A second container carries powdered lyophilized or frozen concentrated antibody or antigen which is the cognate of that on the liposome. A third vial carries powdered or frozen concentrated complement which can be in the form of guinea pig serum and a fourth container carries an enzyme substrate for the enzyme which may be in liquid or powder form. Buffer is also included in another container.

A one-step method can be used where all components are mixed and incubated. However, in some cases, the procedure may be carried out in two or more steps with some of the materials incubated together prior to complete mixing. In all cases, no separation is carried out after the immune reaction or absence of it and a direct reading is made of the reaction materials to determine the presence or absence of the antigen or antibody in the test specimen, by detecting enzyme activity or reaction with the substrate.

It is a feature of this invention that the test can be carried out quickly by untrained personnel at relatively low cost. The readout can be subjective, e.g., visual as by a color change when qualitative readouts are desired. Semi-quantitative readouts may be obtained subjectively, as when deep to light color changes may occur. Spectrophotometric methods and the like can also be used to detect the presence or absence of enzymatic activity in the presence of substrate which indicates lysing of the liposome or immune specific attack on the liposomal membrane so as to expose the enzyme to the substrate. The exposure of enzyme activity will occur when the immune reaction occurs to form an immune complex and affect the bilayer or enzyme enclosing membrane of the liposomes. When the antibody or antigen, as the case may be, in the system reacts with the opposite with which the liposome is labeled in the presence of active complement, the enzyme is released. However, if the test sample contains the antigen or antibody to be tested for, reaction of the cognate in the media prevents or reduces reaction with the cognate label and thus prevents the enzyme from being detected in the substrate indicating a positive for the antigen or antibody being tested for.

BRIEF DESCRIPTION OF PREFERRED EMBODIMENTS

The liposomes of the present invention are sometimes called smectic mesophases or synthetic vesicles. They are in fact dry lipid films suspended in aqueous media as have been described by Uemura, K. and Kinsky, S. C. (1972) Biochemistry 11, 4085-4094. Liposomes are believed to consist of lipid bilayers which separate an internal aqueous compartment from an external aqueous media and are in fact prototypes of biological membranes. The liposomes mimic the properties of biological membranes. As is known, they can be made to contain either enzyme substrates or enzymes. For purposes of the present invention, the liposomes contain an enzyme and have an outer surface substantially free of the enzyme which outer surface encloses the enzyme such that the catalytic action of the enzyme is not detectable unless the outer surface encapsulating the membrane is disrupted and is labeled with an antigen or its cognate antibody depending upon the test to be carried out. Preferably if one is testing for the antibody, the liposome will be labeled with that antibody while if one is testing for the antigen, the liposome will be labeled with the antigen.

Liposomes have been known in the art. However, the art is not believed to have previously obtained liposomes having enzymes contained therein which liposomes have signal to noise ratios of no less than 5. This is probably so since the art has not recognized the advantage of obtaining such liposomes for use in immunoassay procedures.

The signal to noise ratio should be 10 or higher such as preferably at least 60, and can be 1,000 or more so that the liposomes contain and sequester the enzyme from the substrate. Thus no detectable enzymatic activity occurs in the absence of an antigen-antibody complex or immune complex being formed to rupture or render porous the liposome membrane. In some cases, the signal to noise ratio can be 5 or higher in liposomes in accordance with this invention, so long as no detectable enzymatic activity occurs in the absence of an antigen-antibody complex or immune complex being formed. The signal to noise ratio as known in the art is obtained by comparing a first vial or noise vial, of liposome labeled with one of antigen or cognate antibody suspended in an isotonic buffer in the presence of enzyme substrate as compared to a second or signal vial containing enzyme substrate, liposome as previously described, in the presence of a known lysing agent such as a strong detergent. The signal to noise ratio is the test result of the enzyme reaction observed. Preferably the noise tube not containing the lysing agent is as low as possible indicating no noise thus little or no enzyme activity.

Preferably the noise is maintained low or non-existent for as long a time period as possible. In the preferred form, the noise level is at zero or close thereto after storage for at least sixty days or the signal to noise ratio is no less than 10. This gives good shelf life which is desirable when selling test kits for use in the present invention.

In the immunoassay methods of this invention the liposome sequesters the enzyme from the substrate and through the mediation of immunospecifically activated complement, otherwise latent (hidden) enzyme activity becomes apparent. The liposome encapsulates the enzyme, i.e., the enzyme is physically trapped within a space delimited by a bilayer membrane. The physical encapsulation also acts to sequester the enzymatic activity. Para-Nitrophenyl-phosphate (pNPP) is a substrate for the enzyme alkaline phosphatase (AP). Under alkaline conditions (pH greater than 7) AP will snip off the phosphate group from pNPP (which is colorless) producing para-Nitrophenol which under alkaline conditions is intensely yellow colored. Thus, if one prepares an aqueous solution of pNPP, this solution is colorless. If one then adds AP to this solution an intense yellow color is produced quite rapidly. The liposomes used in this invention are such that they encapsulate AP and sequester this AP away from pNPP in the surrounding aqueous solution. Thus, the liposomes with encapsulated AP can be dispersed in pNPP solutions and very little yellow color is produced, while if the same quantity of AP which is encapsulated were to be introduced, directly, considerable color would be developed quite rapidly.

For the above reasons in constructing liposomes, enzymes whose activity can be effectively sequestered by the intact lipid bilayer are selected resulting in a signal to noise ratio greater than 5. It is preferred not to use enzymes which:

(a) would be adsorbed to the other surface of the liposome membrane, and thus at all times accessible to substrate in the surrounding medium.

(b) would be included in the bilayer itself such that it would span both the internal and external media and might likewise be readily accessible to substrate in the surrounding medium.

(c) react with substrates which can readily diffuse through an intact lipid bilayer (typically such would be nonpolar, lipid-soluble, small molecules). In this case even though the enzyme might be encapsulated, its activity would not be sequestered inasmuch as substrate in the surrounding medium, by diffusion through the lipid bilayer, could gain access to the enapsulated enzyme.

The structure of sequestration is important in the context of an immunoassay using the present invention. It is because this sequestration can be broken immunospecifically that one may obtain a homogeneous assay, i.e., it is not necessary to have physical separation of bound from free signal by centrifugation, chromatography, filtration, solid phase immobilization, etc. Such separations are time-consuming, require special instrumentation or apparatus, and are difficult to automate.

Liposomes are prepared from amphiphilic lipids. Lipids may be defined generally as molecules of intermediate molecular weight (150–3,000 daltons) consisting mainly of saturated or unsaturated and/or aromatic or aliphatic hydrocarbon moieties. Amphilic lipids are those which contain both water soluble and water insoluble regions.

Small (J. Am. Oil Chem. Soc. 45, 108–117 [1968]) provides a classification of lipids based upon their interaction with water, both in bulk and at the surface. Such lipids useful in the present invention are defined below:

Class I—Insoluble, Non-Swelling Amphiphilic Lipids di- and triglycerides, long chain protonated fatty acids, sterol esters, long-chain alcohols, phytols, retinals, Vitamin A, Vitamin K, Vitamin E and many sterols such as cholesterol, desmosterol, Vitamin D, and a number of hormones.

Class II—Insoluble, Swelling Amphiphilic Lipids

Lecithins, phosphatidyl ethanolamines, phosphatidyl inositol, sphingomyelin, cerebrosides, phosphatidic acid, plasmalogens, phosphatidyl serine, cardiolipins, and certain plant sulfolipids.

Class III A—Soluble Amphiphiles, Type A

Form liquid crystalline phases when small quantities of water are added (lyoptropic mesomorphism). Includes many of the classic anionic, cationic and nonionic detergents.

Class III B—Soluble Amphiphiles Type B

Will not form liquid crystals, no clear-cut polarity-bile salts.

Class II lipids are particularly appropriate for the formation of liposomes, and the latter can often be prepared from such lipids alone. For example, quite large vesicles can be prepared from phosphatidyl ethanolamine or phosphatidyl serine according to Papahadjopoulos Annals N.Y. Acad. of Sci. 308, 1978. In some cases, however, it is useful to incorporate Class I or Class III lipids into the vesicle bilayer for structural purposes—to produce less fluid bilayers e.g. by incorporation of cholesterol or to promote greater spacing between adjacent bilayers as for example by electrostatic repulsion resultant from the incorporation of anionic-dicetyl phosphate- or cationic-stearylamine lipids into the bilayers. Procedures for preparing a variety of vesicular structures have been described (Szoka and Papahadjopoulos Proc. Nat. Acad. Sci. 75, 4194–4198 [1978]). Many of these structures with appropriate modification can be adapted to the present inventions. In selecting an appropriate mode of preparation, several criteria are preferably applied as follows:

1. The mode of incorporation of enzyme into the liposomes should not result in inactivation or denaturation of the enzyme. Thus, prolonged exposure to elevated temperatures of denaturing organic solvents is to be avoided.

2. The liposomes should be sufficiently large to incorporate enzyme activity. Structures less than 50–100 Å in diameter would not encapsulate more than a few enzyme molecules in most cases and are not preferred.

3. The liposomal bilayer should be stable and relatively impermeable. It has been shown (Kitagawa T. and Inoue K. Nature 254, 254-6 [1975]) that incorporation of Class I lipid such as sterols leads to a condensing of the bilayers with resultant greater rigidity and stability and are more susceptible to complement mediated lysis.

In preparing liposomes, it is necessary that lipids—such as those of Class II—which are insoluble in water be introduced into an aqueous environment. This can be achieved by a variety of methods.

By one such known method, lipids are physically dispersed into an aqueous solution. A dry thin film of lipids is formed on the interior surface of a suitable vessel. The aqueous solution containing the substances to be entrapped within the liposomes is then placed in the vessel in contact with the lipid film. The lipid film is then dispersed into the aqueous solution by vigorous agitation of the vessel (glass beads approximately 0.1 mm in diameter may be included in the vessel to accelerate this dispersion). Also, dispersion of the lipid film may be enhanced by sonication through immersion of the vessel in a bath type sonicator or by immersing the probe of a sonifier into the aqueous solution. Excessive sonication may inactivate enzyme and can produce very small liposomes.

Alternatively, the lipids may be dissolved in an aqueous solution containing a detergent lipid of Class III A or B such as laurylsulfate or sodium deoxycholate. The detergent is then removed (e.g. by dialysis), and the liposome bilayers are formed. Enoch and Strittmatter (Proc. Nat. Acad. Sci. 76, 145-149) have described the preparation of 1000 Å diameter, single-bilayer liposomes using sodium doxycholate as the detergent which is dialyzed.

Another known technique involves the addition of aqueous solution to a mixture of lipid and a volatile organic solvent which solvent is subsequently removed by evaporation at reduced pressure. Szoka and Papahadjopoulos (Proc. Nat. Acad. Sci. 75, 4194–4198 [1978]) have described preparation of liposomes with very large internal aqueous space by means of evaporation of organic solvents diethyl ether or isopropyl ether.

The physical and detergent dialysis methods are particularly appropriate to the present invention, as these produce acceptably large vesicles and are quite gentle, thus unlikely to inactivate the enzymes. In cases where organic solvent evaporation is to be employed, it is necessary that the enzyme to be encapsulated should be insensitive to that solvent. For example, vesicles of this type can be prepared containing alkaline phosphatase which enzyme is not denatured by the diethyl ether used in the process.

Enzymes suitable for use in the present invention include any of those which will result in low noise levels. A large number of known enzymes may be employed in the present invention. These vary widely in their substrates, the nature of the reaction catalyzed, stability, turnover rate, optimal reaction conditions (pH, ionic strength, temperature), and the like. The International Union of Biochemists has classified various enzymes according to the nature of the reaction catalyzed.

There are a number of criteria which may be applied in the selection of a given enzyme for commercial application. These enzymes which are at present available in but trace amounts, are less desirable than those which are abundant and may be purchased from commercial sources. The enzyme should be stable when stored at temperatures which are convenient at the site of commercial application, e.g. 4° C., for a period of at least 3 months. The catalytic activity or turnover number of the enzyme should be sufficiently high as to provide detectable reaction in a relatively short time period, i.e. a few seconds to 120 minutes. The catalytic activity of the enzyme should be conveniently detectable by means available to the commercial user, e.g. the catalyzed reaction produces an increase or decrease in the absorption of light in the ultraviolet or the visible region, i.e. in the range of 250–750 nm.

Preferably the enzyme should be one which is not present at significant levels in the sample to be tested and is not susceptible to inhibition by substances commonly found in the test sample.

The enzyme should not be inactivated or poisoned by the lipids employed in liposome preparation and is not inactivated or denatured during the liposome preparation. The enzyme selected should be one which may be fully encapsulated. Such enzymes in nature are found in the cellular cytoplasm or circulate freely in extracellular fluids. Not desirable are the natural membrane proteins. These in nature are found in association with cellular membranes and have hydrophobic surface(s) which anchor them to the bilayer. Commonly such enzymes span the bilayer with their catalytic sites exposed to the surrounding aqueous medium.

The following table indicates enzymes of particular interest classified according to the International Union of Biochemists:

1. Oxidoreductases
   1.1 Acting on the CH—OH group of donors
      1.1.1 With NAD or NADP as acceptor
         1. alcohol dehydrogenase
         6. glycerol dehydrogenase
         26. glyoxylate reductase
         27. L-lactate dehydrogenase
         37. malate dehydrogenase
         49. glucose 6-phosphate dehydrogenase
         17. mannitol 1-phosphate dehydrogenase
      1.1.2 With cytochrome as an acceptor
         3. L-lactate dehydrogenase
      1.1.3 With $O_2$ as acceptor
         4. glucose oxidase
         9. galactose oxidase
   1.2 Acting on the CH—$NH_2$ group of donors
      1.4.3 With $O_2$ as acceptor
         2. L-amino acid oxidase
         3. D-amino acid oxidase
   1.6 Acting on reduced NAD or NADP as donor 1.6.99 With other acceptors diaphorase
1.10 Acting on diphenols and related substances as donors
   1.10.3 With $O_2$ as acceptor
      1. polyphenol oxidase
      3. ascorbate oxidase
1.11 Acting on $H_2O_2$ as acceptor
   1.11.1
      6. catalase
      7. peroxidase
3. Hydrolases
   3.1 Acting on ester bonds
      3.1.1 Carboxylic ester hydrolases
         7. cholinesterase
      3.1.3 Phosphoric monoester hydrolase
         1. alkaline phosphatase
      3.1.4 Phosphoric diester hydrolase
         3. phospholipase C
   3.2 Acting on glycosyl compounds
      3.2.1 Glycoside hydrolases
         1. $\alpha$-amylase
         4. cellulase
         17. lysozyme
         23. $\beta$-galactosidase
         27. amyloglucosidase
         31. $\beta$-glucuronidase
   3.4 Acting on peptide bonds
      3.4.2 Peptidyl-amino acid hydrolase
         1. carboxypeptidase A
      3.4.4 Peptidyl-peptide hydrolase
         5. $\alpha$-chymotrypsin
         10. papain
   3.5 Acting on C—N bonds other than peptide bonds
      3.5.1 In linear amides
         5. urease
   3.6 Acting on acid anhydride bonds
      3.6.1 In phosphoryl-containing anhydrides
         1. inorganic pyrophosphatase
4. Lyases
   4.1 Carbon-carbon lyases
      4.1.2 Aldehyde lyases
         7. aldolase
   4.2 Carbon-oxygen lyases
      4.2.1 Hydrolases
         1. carbonic anhydrase
   4.3 Carbon-nitrogen lyases
      4.3.1 Ammonia lyases
         3. histidase Substrates useful in this invention include those reactive with the enzymes selected for use as known in the art and thus include for example p-nitrophenyl phosphate and 4-methyl umbelliferyl phosphate for alkaline phosphatase; 4 aminosalicylic acid or o-dianiside and hydrogen peroxide for peroxidase; and o- or p-nitrophenyl glycosides for glycosidases. Other useful substrates include those listed by Bergmeyer, Methods for Enzymatic Analysis, Academic Press N.Y. 1965. Not desirable are those substrates which would readily diffuse through an intact membrane bilayer. Generally such substrates would be small molecules which are soluble in lipid solvents.

Antigens which can be tested for or used as labels for the liposomes in accordance with this invention are numerous. There are a number of antigens, the quantitation of which is of significance in clinical diagnostics. Many of these are now assayed by radioisotopic methods. Assays for these by the present invention would be a considerable improvement inasmuch as hazardous, unstable reagents are not employed.

The present invention would be beneficially applied to the detection and estimation of circulating hormones as indicators of endocrine function. A partial listing of these would include:

thyroid hormones—thyroxine and triidothyronine, parathyroid hormone and calcitonin.

pancreatic hormones—insulin, proinsulin, and glucagon.

pituitary hormones—prolactin, adrenocorticotropic hormone, tyrotropin, oxytocin and vasopressin.

uterine and placental hormones—chorionic gonadotropin, placental lactogens, chorionic thyrotropin and relaxin.

steroid hormones—Estradiol, Estrone, Estriol, Testosterone and Dihydrotestosterone.

growth factors—Urogastrone, Nerve growth factor and the somatomedins.

The method may be usefully applied to the intracellular messengers, the cyclic nucleotides and prostaglandins.

The present invention may also be applied to the screening of circulating levels of therapeutic drugs, e.g. the cardiac glycosides; digoxin, digitoxin, anticonvulsants, diphenylhydantoin, mesantoin, phenobarbital, and mephobarbital. Of particular interest are those drugs with narrow therapeutic index i.e. a certain minimal circulating level is required for therapeutic efficacy while a moderately higher level elicits toxic or harmful reactions.

The procedure may also be adapted to screening for antibiotics such as penicillin, streptomycin, and tetracyclines, chlortetracycline, oxytetracycline, and tetracycline, chloramphenicol, erythromycin, caromycin, polymyxin B. The aminoglycoside antibiotics gentamycin, amikacin, tobramycin, kanamycin and neomicin employed in the management of aerobic Gram negative bacillary infections can be conveniently assayed by the present invention.

This method may also be applied to the detection and estimation of drugs of abuse such as opiates-morphine, heroin, meperidine and methadone; ergot alkaloids, such as lysergic acid diethylamide, marijuana, barbiturates and cocaine and its derivatives.

Inasmuch as the present invention is very simple in performance and does not employ unstable or hazardous reagents, the assay method is applicable in environments which are less well-equipped and sophisticated than diagnostic laboratories. For example, the assay method can be applied to screening food and environmental toxins. In food screening, important antigens would be mycotoxins and natural toxicants. This area involves such major toxins as aflatoxins, ochratoxin, patulin, penicillic acid, zearelonone; and tricothecene toxins, as well as toxic metabolites such as ipomeamerone that occur naturally in foods. Beyond the natural toxicants there are a wide variety of environmental contaminants, the presence of which in foods even in trace amounts poses a significant threat to mankind. These may be industrial byproducts or pesticides e.g. polychlorinated biphenyls, chlorinated dibenzo-p-dioxins, chlorinated dibenzofurans, heptachlorepoxide, dieldrin, and DDT 1,1'-2,2,2-Trichloroethylidene)bis[3-chlorobenzene]; 1,1,1 trichloro-2,2 bis (p-chlorophenyl) ethane.

Other food contaminants of concern are the antibiotics-penicillin, chloramphenicol and tetracycline.

The method need not be restricted to small molecules as it has been shown (Humphries and McConnell Proc. Nat. Acad. Sci. 71, 1691–1694, 1974) that macromolecular antigens such as egg albumin may be coupled to the surface of immunoreactive liposomes. Thus, the present invention may also be applied to detection of macromolecular antigens—plasma proteins, hepatitis associated antigens, histocompatibility markers.

Antigens and antigenic materials which are to be analyzed for purposes of this application include any which by themselves or with other products will produce antibodies cognate therefor and thus detectable by the immune reaction. For example, digoxin is considered an antigen because it with another material will produce antibodies such that the antibody to digoxin can be used in a test with either the antibody or digoxin used as the label depending upon whether one is testing for the digoxin or the cognate antibody. Such materials as bovine serum albumin, key hole limpet heomocyanin or other macromolecular carriers are covalently coupled to the digoxin or other "antigen" in forming antibodies. Thus the word "antigen" as used herein is meant to include all antigenic materials whether antigenic by themselves or in combination with other materials to produce cognate antibodies in animals such as man, rabbits, goats, sheep, guinea pigs, bovine species and other mammals.

The present invention may be employed to detect and quantitate specific antibodies directed against various antigens. The presence as well as the amounts of such antibodies may be taken as indicators of the potential of immunity to various infectious disease, previous exposure to disease, or active infection.

For example, the present invention readily lends itself to the detection of Syphillis antibodies (directed against Treponema Pallidum) as these antibodies are reactive against cardiolipin (extracted from beef heart) which is readily incorporated into liposomes.

Antibodies directed against infectious disease agents—virus, bacteria, parasites may also be detected by coupling the surface antigenic markers from those to the liposome surface.

In some cases, the presence of antibodies directed against specific macromolecule(s) can indicate autoimmune disorders—e.g. antibodies reactive to nucleic acids polydeoxyribonucleic acids and polyribonucleic acids, collagen, gamma globulins, thyroglobulin, parathyroid antigens, mitochondrinal antigens, smooth muscle antigens are all potential indicators of artoimmune diseases.

Antibodies are produced by introducing an immunogenic substance into the bloodstream of a living animal. The animal responds with the production of antibodies which bind to the immunogen as the first step in the detoxification of the immunogen. Many antigens are directly immunogenic and elicit antibody production directly. However, a number of substances are not in themselves immunogenic and require modification (coupling to a suitable carrier). Methods for the production of antibodies are described in considerable detail by Landsteiner Speficity of Serological Reactions, Dover Publications N.Y. 1962 and Weir.

Complement (a group of at least 9 different proteins) is a key component of a hosts immune defense against invading cellular pathogens. Complement, once activated (alerted to the presence of a cellular invader) attaches to the outer membrane and creates small lesions in this membrane. In effect complement carves little holes all over the surface of membrane. These holes are quite small, on the order of 100 Å ($100 \times 10^{-8}$ cm) in diameter. Very small molecules such as water and simple salts may readily diffuse through such lesions. However, macromolecules such as proteins are commonly about the same size or larger than these lesions 40–250 Å, so that such macromolecules cannot diffuse through these lesions or do so exceedingly slowly, see Green H., Barrow P., and Goldberg, B., (1959) J. Exp. Med. 110, 699. In the present invention the complement used permits an antigen antibody reaction to effectively poke holes in the liposome encapsulating layer. It is believed that this permits the substrate to enter the liposome bilayer and react with the enzyme therein. Thus an enzymatic reaction occurs even if no complete lysis of the bilayer occurs. The complement permits the reaction either by aiding in lysis or acting to form the holes which permit reaction without lysis. The term "lysis" is used herein to denote the breakdown and complete rupture of the liposome bilayer as well as the exposure of the encapsulated enzyme to substrate through holes formed in the bilayer by the immune reaction.

In a typical kit to detect antigen, a vial contains a liposomes labeled with an antigen suspended in an appropriate buffer, as for example in a volume of from 0.1 to 10 ml. The concentration of the liposome in the buffer will normally vary from 1 to 50 millimolar. Useful buffers include phosphate buffered saline or other isotonic buffer. A second vial contains lyophilized powder form or frozen concentrate of the cognate antibody to the antigen. In the case where antibody is to be detected by the direct method, this vial would represent the positive control for the assay. A third vial contains lyophilized powder or frozen concentrate of complement. Conventional complement for the antigen-antibody complex to be formed is used as known in the art. For example, such complement can be guinea pig serum. Another vial contains the enzyme substrate which can be a liquid, powder, or the like, at a sufficient concentration to enable ease of detection of enzymatic activity if the enzyme contained within the liposome is released. Another vial can contain a buffer to use in diluting the materials during the tests of this invention.

In the simplest and most preferred test, all of the materials including the substrate are added to a single vial, incubated and a color change or the absence of a color change is detected to determine whether or not the test material which can, for example, be serum of an individual, contains or does not contain a specific antigen or antibody. In some cases, all of the materials except the substrate are added to a single vial, incubated and then admixed with enzyme substrates and a color change or the absence of a color change is detected to determine whether or not the test material which can, for example, be serum of an individual, contains or does not contain a specific antigen or antibody. Particularly desirable enzymes are alkaline phosphatase and peroxidase because their reaction with p-nitrophenyl phosphate and 4-aminosalicylic acid give color reactions easily detectable to the eye.

In cases where inhibition of complement lysis is employed for analyte quantitation, there are some limitations on the order of addition. This results from the fact that once liposomes bearing antigen or antibody, complement, and the partner antibody or antigen are brought together, lysis begins. For purposes of quantitation accuracy, it is preferred that the sample to be analyzed be added to the vial before the complement can act. Thus, useful orders of addition would be: (1) antibody, (2) liposomes, (3) sample, (4) complement. Entries 1, 2 and 4 can be permuted but sample is preferably always added before antibody complement and liposomes are combined.

In all cases, it is preferred to include a known positive test to be run as a check with the test. For example, if the test is a test for digoxin, a standard digoxin vial will be included in the test kit. Where the test is to be a quantitative test as well as a qualitative test, the test kit can include several samples of the material being tested at different concentrations, so that the color change obtained, if any, in the test sample can be compared with the color change or other enzymatic activity of each standard sample when the standards are tested along with the test sample in an analytic procedure.

The determination of enzyme activity is well-known for a large variety of enzymes. Such known tests can be used to monitor enzyme activity following testing in accordance with this invention. A list of assay methods for many of these is given by Bergmeyer, Methods for Enzymatic Analysis, Academic Press N.Y. 1965. Most favored amongst the types of assays would be these which offer either high sensitivity or convenient packaging.

To determine activity of malate dehydrogenase (E.C. 1.1.1.40) the enzyme is reacted with substrates L-malic acid and nicotinamide adeninine dinucleotide and the progress of the reaction is monitored at 340 nm as in the following procedure:

Into cuvettes are placed the following:

|  | Test | Control |
|---|---|---|
| Phosphate buffer | 2.6 ml | 2.7 ml |
| NADH$_2$ | 0.2 ml | 0.2 ml |
| Enzyme (diluted) | 0.1 ml | 0.1 ml |
| Substrate | 0.1 ml | — |

Enzyme—dilute with 0.1M phosphate buffer, pH 7.4, to a concentration of 0.1–0.3 units/ml.
Substrate—0.006M oxaloacetate (freshly prepared). Dissolve 6.7 mg of the acid in 1 ml phosphate buffer (1.0M pH 7.4), titrate to pH 7.4 with NaOH, and make to volume of 10 ml.
NADH$_2$—0.00375M. Dissolve 50 mg of NADH$_2$ and 240 mg of THAM in 15 ml of H$_2$O, titrate to pH 7.4 in HCl, and make to volume of 20 ml.
Phosphate buffer—0.1M, pH 7.4.

Prior to adding the substrate, the instrument is balanced with control cuvette at an absorbancy of 0.200. Readings are taken at 15-second intervals for 2 minutes and the initial rate of change of absorbancy per minute is determined.

This enzyme has a very high turnover number, and therefore, lends itself to highly sensitive assays.

Many other enzyme assays could be selected because they lend themselves to convenient assay formats or substrate packaging. Amongst these are:

Alkaline Phosphatase (E.C. 3.1.3.1). The synthetic substrate p-nitrophenylphosphate is used and this can be conveniently packaged in capsule form.

Pipette 3.0 ml of substrate into each of two 1-cm cuvettes. Adjust spectrophotometer to read zero absorbancy at 410 m$\mu$.

Enzyme—dilute with water to contain approximately 0.005 mg/ml. mg/ml=A$_{278}$×1.43 (Plocke, et al, 1962)
Substrate—0.001M p-nitrophenyl phosphate in 1.0M Tris buffer, pH 8.0

At zero time, add 0.1 ml of enzyme solution to test cuvette and record absorbancy change. Molar absorbancy index for p-nitrophenol in 1.0M Tris, pH 8.0, is 1.62×10$^4$. One unit is that activity liberating one micromole p-nitrophenol per minute under the defined conditions at 25° C. In this reaction a yellow-colored product is formed which is detectable by direct visual examination.

Also useful because of its widespread availability is the enzyme horseradish peroxidase (E.C. 1.11.1.7). A multiplicity of substrates and assay formats are available for this enzyme. One example is:

Add 0.05 ml of dye to 6.0 ml of substrate. Transfer 2.9 ml to test cuvette and pour remainder into control cuvette. At zero time add 0.1 ml of diluted enzyme. Introduce the enzyme into the cuvette from a 0.1 ml pipette with the tip below the surface. Mix by inverting cuvette with wax paper over top. Record absorbancy at 15-second intervals for 1-2 minutes and determine rate of change per minute.
Substrate—Stock: 1 ml of 30% H$_2$O$_2$ (Merck's Superoxol) diluted to 100 ml with H$_2$O. To use, dilute 1 ml of stock H$_2$O$_2$ to 100 ml with 0.01M phosphate buffer, pH 6.0 (fresh daily).
Dye—1% o-dianisidine in methyl alcohol (fresh, in amber bottle).
Enzyme—Stock solution: 1 mg/ml in water. Immediately before using, dilute 0.1 ml to 250 ml.

One unit of peroxidase activity is that amount of enzyme decomposing 1 micromole of peroxide per minute at 25° C.

In order for the liposomes to function in immunoassay, it is necessary that they be sensitized and labeled at their surface with the appropriate antigens. Antigens may be covalently bonded or in some cases absorbed to the surface of preformed liposomes. Alternatively, the antigen may be covalently linked to an appropriate amphiphile and this complex included in the lipid mixture from which the liposomes are formed. In the latter case, the amphiphile is incorporated into the lipid bilayer, and the attached antigen extends into the surrounding aqueous solution.

When liposomes are preformed, they can have at their external surface several chemical functionalities to which antigens may be covalently linked. Foremost amongst these are: amino groups derived from phosphatidyl ethanolamine, hydroxyl groups provided by phosphatidyl inositol, and carboxyl groups provided by fatty acids or phosphatidyl serine. These are precisely the functionalities available on proteins which are exploited in coupling small antigens to produce immunogens. Thus, antigens may be coupled to preformed liposomes by traditional chemical reactions—using bifunctional coupling agents such as: glutaraldehyde, diimide esters, aromatic and aliphatic diisocyanates, Bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinifrodiphenyl sulfone. Appropriate reactions which may be applied to such couplings are described in Williams et al Methods in Immunology and Immunochemistry Vol. 1, Academic Press, New York 1967.

In some cases, antigens may be absorbed to the liposome surface. Such is the case with certain lipopolysaccharides as was shown by Uemura and Kinsky (Biochemistry 11, 4085-4094 1972). This also obtains for antigens coupled with the Class III amphiphile lysolecithin.

The fact that an antigen may first be coupled to a selected amphiphile e.g. phosphatidyl—ethanolamine, serine—or inositol—and then included in the lipid mixture from which the liposomes are formed is most relevant inasmuch as this coupling reaction may be performed in a variety of solvents. In coupling antigens to preformed liposomes or to proteins (as in preparing antigen), the reaction must almost always be performed in aqueous solutions as organic solvents will inactivate or denature or rupture proteins or liposomes. For example, if one wishes to couple an antigen containing a carboxyl residue, one may prepare the acid chloride of the antigen using thionyl chloride. This acid chloride may then be coupled to phosphatidyl ethanolamine in benzene as solvent. This flexibility in choice of solvent will permit a broad range of antigens to be coupled to the liposomes.

The following Examples are given to illustrate the present invention and are not to be considered as limiting thereof.

EXAMPLE I

To prepare immunoreactive liposomes labeled at their surface with dinitrophenyl groups, a mixture containing 40 milligrams of L-α-lecithin (Products #P5763 Sigma Chemical Co. of St. Louis, Mo.) 11.6 mg of cholesterol (Products #CH-S Sigma Chemical Co. Lot 57C-7190), 2.18 mg of dicetyl phosphate (Product #D 2631 Sigma Chemical Co. lot 28 [0460]) and 2 mg of N-dinitrophenyl aminocaproyl phosphatidylethanolamine (Avanti Biochemicals of Birmingham, Ala., lot DCPE 17) in 6 milliliters of chloroform was prepared. Solvent was evaporated under reduced pressure (water aspirator) in a 50 ml flask on a rotary evaporator producing a thin film of dry lipid on the interior surface of the flask. In order to insure complete removal of the solvent, evaporation was continued for 30 minutes beyond the point where the lipid film was visibly dry. A solution of 4 milligrams of alkaline phosphatase (E.C. 3.1.3.1) in 4 ml of 0.01M phosphate buffer pH 7.5 containing 0.3M glucose was added to the flask which was purged and sealed under argon. The sealed flask was gently swirled to disperse the lipid film. The lipid film gradually disappears from the surface of the flask and the aqueous phase grows progressively turbid. At this point, the flask is held at 4° C. for 2 hours. Liposomes containing entrapped alkaline phosphatase are then separated from free enzyme by centrifugation at 27,000 g for 60 minutes. The liquid supernatant is decanted and the pellet containing the liposomes is resuspended in isotonic saline buffer (0.01M phosphate pH 7.5 containing 0.15M sodium chloride). Further purification is obtained by repeated centrifugation and resuspension.

The extent to which enzyme is encapsulated within such liposomes is measured by detergent lysis assay. In the presence of the detergent Triton X-100, a product of Rohm and Haas Co. which acts as a detergent, the liposomes are ruptured and the contents are liberated. A 10 μl aliquot of the purified liposomes is added to 1 ml of 1% Triton X-100 in deionized water. As a control, 10 μl of liposomes are added to 1 ml of isotonic saline. Enzyme is then measured by adding 50–100 μl aliquots of these dilutions to 1 ml of a solution of 0.4 mg/ml of the substrate paranitrophenyl phosphate in 0.1M borate pH 9.0. The hydrolysis of substrate is monitored by the appearance of paranitrophenol and increasing absorbance of light at 410 nm. This reaction is allowed to proceed for 10 minutes and is then terminated by the addition of 1 ml of 2N NaOH. The enzyme activity produced by the detergent lysis is compared to the control as a measure of the signal to noise characteristic of the liposomes. For the preparation described, this ratio exceeded 150 i.e. the absorbancy increase produced in 10 minutes by the detergent lysed liposomes was 1.5, the control produced less than 0.01 unit of absorbancy increase.

In subsequent experiments, similar liposomes were purified by gel filtration chromatography rather than centrifugation. Three ml of the liposome preparation was layered over a column 40×1 cm of Sephadex G-200 equilibrated with phosphate buffered saline. The liposomes were then eluted from the column appearing with the void volume (approx. 15 ml), well separated from free enzyme which emerged at 30 ml.

EXAMPLE II

Liposomes are prepared by a detergent dialysis method. A dry film from a mixture of 50 mg egg lecithin 3.5 mg cholesterol and 0.5 mg dinitrophenyl aminocaproylphosphatidyl ethanolamine in chloroform was prepared as described in Example I. To this film was added 5.5 ml of solution containing 1 mg/ml of alkaline phosphatase in 0.05M sodium phosphate buffer pH 7.5, along with 3.6 ml of 10 mM sodium deoxycholate in water. The flask containing this mixture was placed in a sonicator bath at 35° C. for 5 minutes and sonicated under argon. A transparent opalescent suspension was obtained. The deoxycholate detergent was then removed by diafiltration using a Millipore Immersible separator. Thirty volumes of 0.05M phosphate pH 7.5 were exchanged into the suspension while maintaining a constant volume of 9.1 ml. The liposomes were then further purified by gel filtration chromatography as described in Example I. In this case, a signal to noise ratio of 225 was obtained.

EXAMPLE III

In this Example, we sought to show that with appropriately prepared liposomes, antibodies directed against a specific antigen could be detected by liberation of enzyme activity concomitant with immune specific lysis. Multilamellar vesicles are prepared as described in Example I and labeled with N-dinitrophenyl aminocaproyl phosphatidyl ethanolamine (5% of lecithin concentration). Five μl of these were mixed with 100 μl of complement (guinea pig serum) 345 μl of a buffer consisting of 50 mM tris (hydroxymethyl) aminomethane pH 7.5 containing 0.15M sodium chloride, 0.15 mM calcium chloride and 0.5 mM magnesium chloride and 50 μl of various dilutions of rabbit antiserum to dinitrophenylated bovine serum albumin. As controls there were included mixtures in which normal rabbit serum replaced the immune serum. As a further control mixtures were prepared in which the complement had been inactivated by incubation at 56° C. for 30 minutes were also prepared. These mixtures were incubated at 25° C. for 15 minutes at which point 100 μl aliquots were removed and added to tubes containing 1 ml of a solution of 0.4 mg/ml paranitrophenylphosphate in 0.1M sodium borate pH 9.0. These tubes were incubated for 5 minutes at 25° C. The phosphatase reaction was then terminated by the addition of 1 ml of 2M sodium hydroxide. The absorbance of the several tubes at 410 nm was then determined spectrophotometrically. The greater the absorbance, the more phosphatase which had been liberated and the greater the extent of immune specific lysis.

| MIXTURE | ABSORBANCE AT 410 nm |
|---|---|
| Control: | |
| Mixture containing non-immune (normal) rabbit serum | .01 |
| Control: | |
| Mixture containig heat-inactivted (normal) rabbit serum | .01 |
| Test mixture containing antiserum to dinitrophenylated bovine serum albumin | 1.2 |

EXAMPLE IV

In this Example, the immune specific lysis of liposomes is applied to the determination of relative concentrations of specific antibody. All conditions were identical to those of Example III but various dilutions of the DNP-BSA antiserum were employed in order to assess the effect of different antibody concentrations upon the extent of complement mediated lysis.

The extent of absorbance increase at 410 nm in 5 minutes was recorded at various dilutions.

| Antiserum Dilution | 410 |
|---|---|
| 1:50 | 1.5 |
| 1:75 | 1.4 |
| 1:100 | 1.15 |
| 1:200 | .65 |
| 1:300 | .30 |

Thus, this method can be employed to assess specific antibody levels.

EXAMPLE V

To test whether antigen would inhibit complement mediated lysis and whether such inhibition could be employed to quantitate antigen levels in a test sample, the protocol of Example III was modified to allow for inclusion of 50 μl. of DNP-Lysine solutions at various concentrations in the initial incubation mixture. If the absorbancy increase at 410 nm in the absence of free DNP-Lysine is taken as 100% lysis, then at various levels of free antigen the following percentages of lysis were recorded:

| Free DNP-lysine (picomoles) | % Lysis |
|---|---|
| 6 | 83 |
| 9 | 69 |
| 13.5 | 56 |
| 18 | 48 |
| 27 | 33 |
| 36 | 23 |

Over this range, there is a linear relationship between the percent lysis and the logarithm of the antigen concentration. Analyzed by linear least squares regression the linear relationship is characterized by the following parameters:
slope= −33.3
y intercept=143
correlation coefficient=0.998
50% occurs at 16.2 picomole.

EXAMPLE VI

Quantitative immunoassay is performed according to a one-step format, i.e. all reagents including enzyme substrate are mixed together at once so that lytic and enzymatic reactions occur coterminously. Such a single step format is simple in practice and can be easily automated.

Twenty-five milligrams of L-α-Lecithin-Dipalmitoyl (Calbiochem-Behring Corp., LaJolla, Calif.) 8.6 mg cholesterol (Sigma), 1.6 mg dicetyl phosphate (Sigma), and 1.5 mg of Dinitrophenyl aminocaproyl phosphatidyl ethanolamine (Avanti) were mixed in chloroform solvent. The solvent was removed under reduced pressure in a rotary evaporator, and a thin film of lipids was formed on the interior of a 50 ml. round bottomed flask. This film was then dispersed in an aqueous solution containing 5 milligrams of alkaline phosphatase (Sigma) in 3 ml. of PBS-Dextrose buffer. The liposomes were then harvested by centrifugation as in the previous examples.

To a single tube were added 2 microliter of these liposomes (20 nanomole of phospholipid), 100 microliter of guinea pig complement (diluted 1.8 in complement lysis buffer, 50 microliter of Rabbit antiserum to DNP, 100 microliter of buffer or standard solution and 1 ml. of phosphatase substrate. The reaction mixture was incubated at 37° C. for ten minutes whereupon 1 ml. of 0.5N sodium hydroxide was added to terminate the enzyme reaction. The absorbance at 405 nm was obtained spectrophotometrically. The extent of reaction was dependent on the quantity of DNP-Lysine (Sigma) as follows:

| Amount of DNP-Lysine (pmole) | Abs. at 405 nm |
|---|---|
| 0 | .95 |
| 2.0 | .902 |
| 2.5 | .811 |
| 4 | .573 |
| 5 | .430 |
| 6 | .311 |
| 7 | .257 |

In the absorbance at 405 nm is plotted against the logarithm of the amount of DNP-Lysine a straight line is derived with slope-66.8, intercept 143 and correlation coefficient 0.995. Fifty percent inhibition of lysis is achieved with 4 pmole of DNP-Lysine.

EXAMPLE VII

In an example of kinetic mode quantitation liposomes as described in the previous example are applied to quantitation of antigens by measuring the rate of the enzymatic reaction. In this case the reagents in quantities described in Example VI are mixed in a spectrophotometer cuvette. The time course of the enzymatic reaction may then be monitored directly. After a characteristic lag phase, the rate of increase in absorbance at 405 becomes a linear function of the free antibody concentration. Typically, one adds to a spectrophotometer cuvette 0.75 ml. of phosphatase substrate solution, 50 microliter of antibody, 0.1 ml. of complement and 5 microliter of liposomes. The cuvette is then a thermostatted spectrophotometer and the absorbance at 405 nm is recorded. A characteristic lag phase of 2–3 minutes occurs during which the absorbance changes slightly. After this lag, the absorbance increases rapidly. Beyond 5 minutes, the rate at increase is a function of the amount of antibody available.

Proteins and other macromolecules can be coupled to liposomes. Such liposomes with proteins attached to the outer surface are susceptible to complement mediated lysis in the presence of antibodies to the attached proteins. Liposomes can be prepared having within the membrane bilayer lipids suitable for coupling with proteins and other macromolecules. Typically, lipids such as phosphatidyl ethanolamine, phosphatidyl serine or phosphatidyl inositol would be suitable.

EXAMPLE VIII

The method described in Example I is employed to prepare liposomes containing alkaline phosphatase. In this case the lipid mixture consists of 25 milligrams of dipalmitoyl phosphatidyl choline, 10 milligrams of phosphatidyl ethanolamine and 8.6 milligrams of cholesterol. These liposomers are purified by repeated centrifugation after which they are resuspended in 2 ml. of 0.1M borate buffer pH 8.5. To this suspension is added 20 microliter of 25% glutaraldehyde. After 10 minutes at room temperature, the mixture is dialyzed overnight against 2 liters of borate buffer. The activated liposomes are then added to 2.4 milligrams of bovine serum albumin in 1 ml. borate buffer. The mixture is then incubated overnight at 4° C. whereupon the liposomes with protein attached are separated from unbound protein by centrifugation at 25,000 g for 30 minutes. Following the assay method described in Examples III and IV and using rabbit antibody to bovine serum albumin, an immune lysis assay can be prepared which will detect albumin in samples quantitatively in the range of from 0.1 to 2 μg 1 ml.

EXAMPLE IX

In order to assay the cardiac glycoside-digoxin was coupled to dipalmitoylphosphatidylethanolamine. To this end mixture containing 0.5 grams (0.64 mmole) of Digoxin in 20 ml. of Ethanol/Dioxane (4:1, v/v) was added to 60 ml. of 0.1M sodium metaperiodate. The mixture was stirred for 30 minutes at room temperature whereupon 4.5 ml. of ethylene glycol was added. This mixture was stirred for one-half hour at room temperature and evaporated under reduced pressure. The resultant solid was then extracted 3 times with 50 ml. of chloroform. The extracts were pooled (total volume 150 ml.) and solvent evaporated under reduced pressure, producing 0.9 gm of oily residue. Twenty-five mg of this crude product of digoxin dialdehyde in 1 ml. of ethanol/chloroform (1:4) was added to 20 mg of dipalmitoylphosphatidylethanolamine in 1 ml of ethanol/chloroform (1:2). Four drops of triethylamine were added and the reaction mixture (pH 9) was incubated overnight at 37° C. and finally evaporated to a dry residue under reduced pressure. This residue was suspended in 2 ml. of ethanol/chloroform (1:1) and 4 milligram of sodium borohydride was added. This mixture was stirred for 30 minutes and then evaporated to dryness under reduced pressure. This residue was then triturated with ethanol and filtered to give a filtrate which upon evaporation yielded 45 milligrams of dipalmitoylphosphatidylphosphatidylethanolamine-digoxin conjugation product.

EXAMPLE X

The conjugate of digoxin and dipalmitoylphosphatidylethanolamine is employed to prepare liposomes with digoxin. In this case 22 milligrams of dimyristoylphosphatidyl choline, 8.6 milligrams of cholesterol, 1.6 milligrams of dicetylphosphate, and 2.5 milligrams of Digoxin-dipalmitoylphosphatidylethanolamine conjugate were dissolved in 3 ml. of chloroform. Solvent was evaporated under reduced pressure and the lipids deposited as a thin film on the internal wall of a 100 ml. round-bottomed flask. The lipid film was then dispersed in (solution as in Example I lines 8–10 and purified also as in Example I).

Assays were performed as in Example VI. Inhibition by digoxin in test samples was observed in range of 0.5–10 ng/ml digoxin in the test sample.

Liposomes can be frozen successfully if they are first suspended in an isotonic medium—0.01M phosphate buffer containing 0.15M sodium chloride. Also useful are solutions buffered in the range from pH 4 to pH 10 containing 0.3M glucose or like carbohydrate. However, liposomes frozen in proteinaceous media e.g. containing bovine serum albumin of rabbit gamma globulins are not preferred as these show elevated levels of enzyme activity in the absence of lytic reagents—detergent or complement plus antibody. Best results are achieved with rapid freezing at a rate of at least 5° C. per minute. Prior to freezing liposomes are suspended in isotonic media at concentrations of 1–10 mg/ml. For example liposomes prepared as in Example I are suspended in 0.01M sodium phosphate buffer containing 0.15M sodium chloride. This suspension contains 2.5 mg of total lipid in 1 ml of liquid. 0.1 ml aliquots of this mixture are placed in a 5 ml. vial. These are then frozen to −20° C. at a rate of 5° C. per minute. The liposomes can be thawed and used after long periods of storage.

While specific embodiments of this invention have been shown and described, it will be understood that many variations are possible. Particular concentrations, combinations and materials can vary greatly so long as the signal to noise ratio minimums of the invention are maintained which aids in preventing false readings. A wide variety of materials can be tested in a wide variety of high volume screening test by relatively unskilled personnel. The material to be tested can be body fluids or mixtures of all kinds. When serum is tested it is preferably treated chemically and/or with heat to remove undesirable inhibition. Prior treatment with amino groups is one such chemical method. Typically, 0.1 ml of 2.54M ammonia is added to 1.9 ml of serum which is then neutralized by the addition of 0.1 ml of 2.54M hydrochloric acid. Also sulthydryl blocking reagents can be useful. In this case 0.1 ml of 0.2M mercaptoethanolin phosphate buffered saline is added to 1 ml of serum. Then 1 ml of 0.2M iodoacetamide is is added. Similarly useful is the sulfonic acid azo dye chlorazol fast pink which selectively inhibits human complement activation but not guinea pig complement. Heat treatment of at least about 58° C. for at least 30 and preferably 60 minutes is also useful to prevent unwanted inhibition of the complement reaction.

What is claimed is:

1. An immunoreactive, stable liposome labeled with one of an antigen or its cognate antibody said liposome sequestering an enzyme carried within it, and having a signal to noise ratio of no less than 5 to 1.

2. A liposome in accordance with the liposome of claim 1, wherein said liposome is formed of a lipid which is a member of the group consisting of water insoluble, swelling amphiphiles of Class II with a sterol and similar Class I non-swelling amphiphiles 3. An immunoreactive, stable liposome in accordance with claim 1 wherein said signal to noise ratio is no less than 60 to 1.

4. An immunoreactive, stable liposome in accordance with claim 1 wherein said signal to noise ratio is no less than 10 to 1.

5. A liposome in accordance with claim 1 wherein said enzyme is selected from the group consisting of oxidoreductases, hydrolases and mixtures thereof.

6. A liposome in accordance with claim 5 wherein said enzyme is selected from the group consisting of alkaline phosphates, peroxidase, malate dehydrogenase and mixtures thereof.

7. An immunoreactive, stable liposome in accordance with claim 1 and having in combination therewith the other of said antigen or cognate antibody.

8. An immunoreactive, stable liposome in accordance with claim 7 and further comprising a plurality of like liposomes being combined in the presence of a substrate for said enzyme with said liposomes being uniformly dispersed in said substrate.

9. A liposome in accordance with claim 8 wherein said signal to noise ratio is in the range of from 5-1000:1.

10. A liposome in accordance with claim 8 wherein said antigen is of use in clinical diagnostics.

11. An immunoreactive, stable liposome in accordance with claim 8 wherein said signal to noise ratio is no less than 10 to 1.

12. A liposome in combination as set forth in claim 8 and further comprising said liposomes being labeled with an antigen.

13. An immunoreactive, stable liposome in accordance with claim 12 wherein said signal to noise ratio is no less than 10 to 1.

14. A liposome as set forth in claim 8 and further comprising said liposomes being labeled with said cognate antibody.

15. An immunoreactive, stable liposome in accordance with claim 14 wherein said signal to noise ratio is no less than 10 to 1.

16. An immunoassay test kit for detecting an antigen or its cognate antibody in a test sample,
said test kit comprising,
a container carrying stable liposomes labeled with one of antigen or its cognate antibody which is to be the subject of the test determination, said liposomes sequestering an enzyme carried within them while having a signal to noise ratio of no less than 5 to 1, said enzyme being substantially contained within said liposomes and shielded from unwanted exposure to surrounding media.

17. An immunoassay test kit in accordance with claim 16 wherein said enzyme has a signal to noise ratio of no less than 10 to 1.

18. An immunoassay test kit in accordance with claim 16 and further comprising a container carrying a substrate for said enzyme which substrate is capable of rapidly engaging and reacting with said enzyme on forming holes in said liposome,
and a container carrying complement for said antibody or antigen.

19. An immunoassay test kit in accordance with claim 18 and further comprising
a container carrying said cognate antibody or said antigen.

20. An immunoassay test kit in accordance with claim 18 and further comprising
a predetermined concentration of said cognate antibody or said antigen and acting as a quantitative mechanism for carrying out an immunoassay test.

21. An immunoassay test kit in accordance with any of claims 18 to 20 wherein said signal to noise ratio is no less than 60 to 1.

22. An immuno test method for determining antigen or its cognate antibody, the steps comprising combining a stable liposome labeled with one of the antigen or its cognate antibody, said liposome sequestering an enzyme carried within it and having a signal to noise ratio of no less than 5 to 1, with a substrate and a material to be tested along with an aget for permitting rapid exposure of the substrate to the enzyme under the test conditions whereby some of said exposure may occur within said liposome and can be visually detected.

23. A test method in accordance with the test method of claim 22 wherein said method is a homogeneous test method.

24. An immuno test method for determining antigen or its cognate antibody, said liposome sequestering an enzyme carried within it and having a high signal to noise ratio of no less than 5 to 1, with a substrate and a material to be tested along with an agent for permitting rapid exposure of the substrate to the enzyme under the test conditions whereby some of said exposure may occur within said liposome,
and determining the presence or absence of an interaction between said enzyme and substrate.

25. An immuno test method comprising forming a mixture of
(a) a stable liposome labeled with one of an antigen or its cognate antibody carrying within it an enzyme and having a signal to noise ratio of no less than 5 to 1;
(b) a substrate for said enzyme and a buffer
(c) a test material to be tested for specific activity of the other of said one antigen or cognate antibody; and
(d) complement,
and detecting the presence or absence of enzymatic activity in said mixture in a homogeneous phase.

26. A test method in accordance with claim 25 and further comprising incorporating in said mixture the other of said antigen and cognate antibody to test for presence or absence of said one cognate antibody.

27. An immuno test method in accordance with claim 25 wherein all of said components form a liquid mixture.

28. An immuno test method comprising forming a mixture of
(a) a stable liposome labeled with one of an antigen or its cognate antibody said liposome sequestering an enzyme carried within it and having a signal to noise ratio of no less than 5 to 1;
(b) a substrate for said enzyme and a buffer
(c) a test material to be tested for specific activity of the said one antigen or cognate antibody; and
(d) complement,
and detecting the presence or absence of enzymatic activity in said mixture under conditions which permit an immune reaction to expose said enzyme to said substrate.

29. The test method of claim 28 wherein said detecting is carried out in a homogeneous phase without the need for mechanical separation or purification steps.

30. An immuno test method in accordance with claim 28 wherein all of said components form a liquid mixture.

31. A test method in accordance with claim 28 and further comprising incorporating in said mixture the other of said antigen and cognate antibody to test for presence or absence of said one cognate antibody.

32. The test method of claim 31 wherein said detecting is carried out in a homogeneous phase.

* * * * *